US007704208B2

(12) United States Patent
Thiele

(10) Patent No.: US 7,704,208 B2
(45) Date of Patent: Apr. 27, 2010

(54) SYNCHRONIZING A SWIVELING THREE-DIMENSIONAL ULTRASOUND DISPLAY WITH AN OSCILLATING OBJECT

(75) Inventor: Karl Thiele, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1097 days.

(21) Appl. No.: 10/558,728

(22) PCT Filed: May 27, 2004

(86) PCT No.: PCT/IB2004/050793

§ 371 (c)(1),
(2), (4) Date: Nov. 29, 2005

(87) PCT Pub. No.: WO2004/106970

PCT Pub. Date: Dec. 9, 2004

(65) Prior Publication Data

US 2007/0032724 A1 Feb. 8, 2007

Related U.S. Application Data

(60) Provisional application No. 60/475,300, filed on Jun. 3, 2003.

(51) Int. Cl.
*A61B 8/00* (2006.01)
(52) U.S. Cl. .................................................. 600/443
(58) Field of Classification Search ................ 600/443, 600/437, 463, 439, 461; 601/1–4
See application file for complete search history.

(56) References Cited

U.S. PATENT DOCUMENTS

| 5,159,931 | A | * | 11/1992 | Pini ........................... 600/443 |
| 5,997,479 | A | | 12/1999 | Savord et al. |
| 6,013,032 | A | | 1/2000 | Savord |
| 6,126,602 | A | | 10/2000 | Savord et al. |
| 2004/0066389 | A1 | * | 4/2004 | Skyba et al. ................. 345/619 |

* cited by examiner

*Primary Examiner*—Eric F Winakur
*Assistant Examiner*—Lawrence N Laryea

(57) ABSTRACT

An ultrasound image display method and System for a two-dimensional monitor (40) that synchronizes a swiveling or rotating volumetrically rendered three-dimensional ultrasound image (76) with the oscillation of an oscillating ultrasound object (72), such as a beating heart or breathing lung. The invention includes swiveling instructions for repetitively swiveling the volumetric ultrasound image (76) in three-dimensional space. Oscillation frequency measuring instructions (108) measure the oscillating ultrasound object's oscillation frequency. Synchronization instructions (118) synchronize a repetitive rotation of the object with the oscillation frequency such that at a predetermined point the beginning of a rotation repetition (110) coincides with the beginning of an oscillation. The volumetric ultrasound image display (76) provides the options of a live display, a variably static display, and pre-recorded display capable of continuous replay.

28 Claims, 9 Drawing Sheets

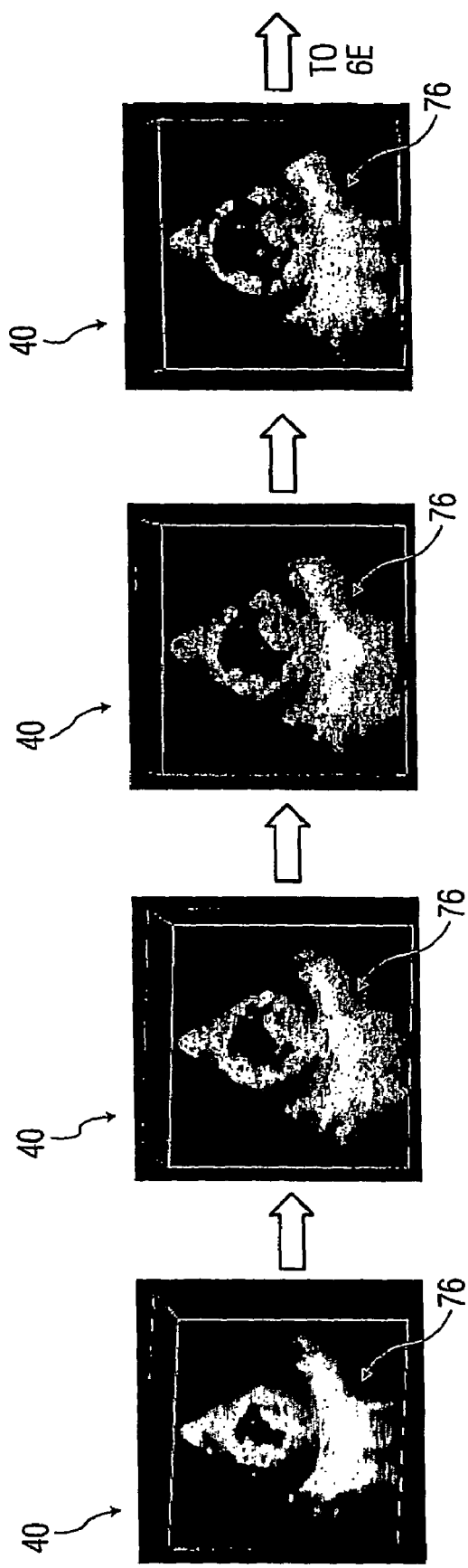

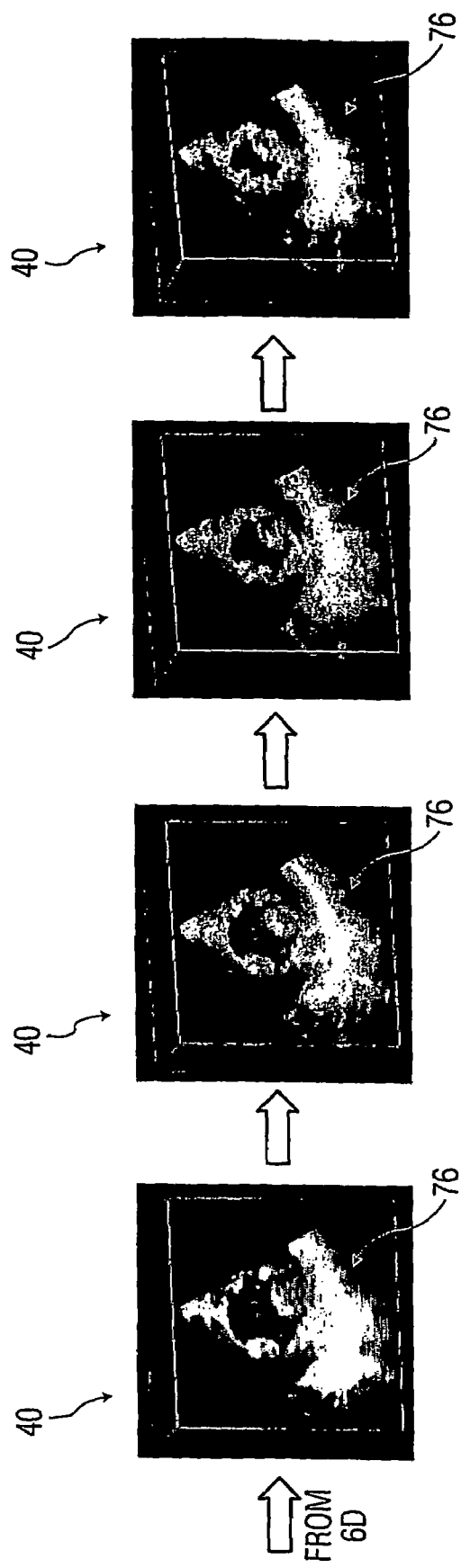

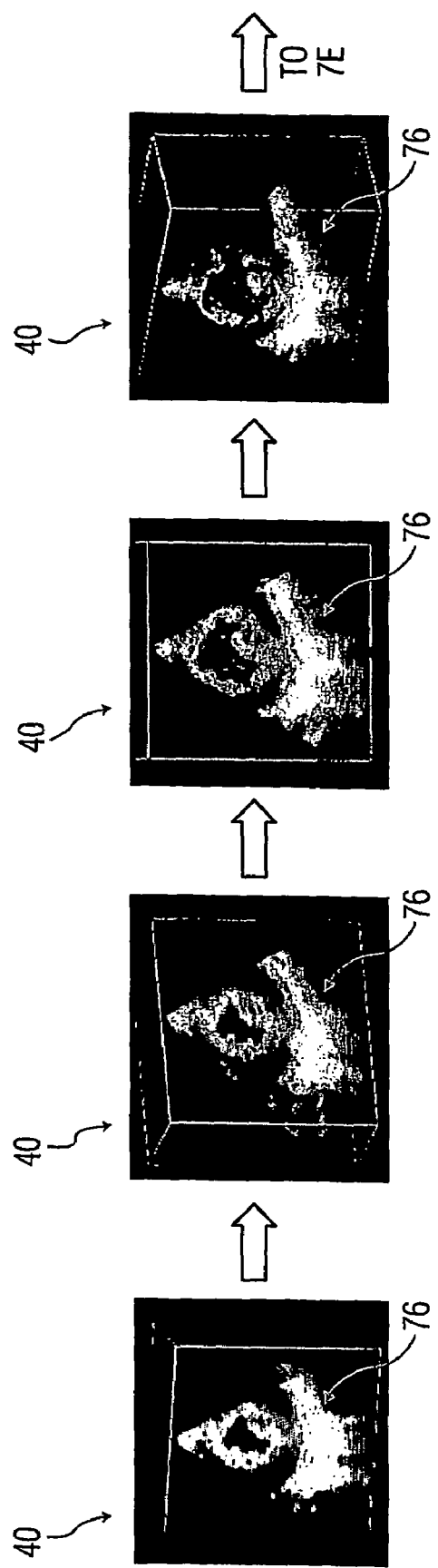

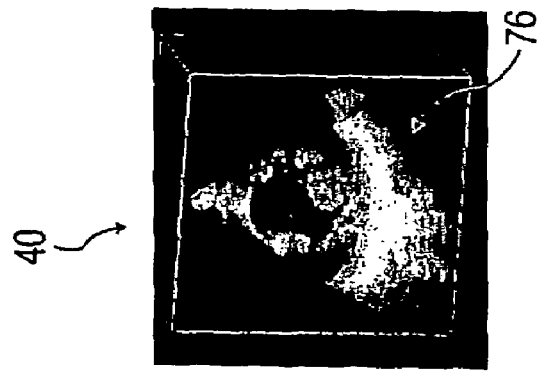
FIG. 7G
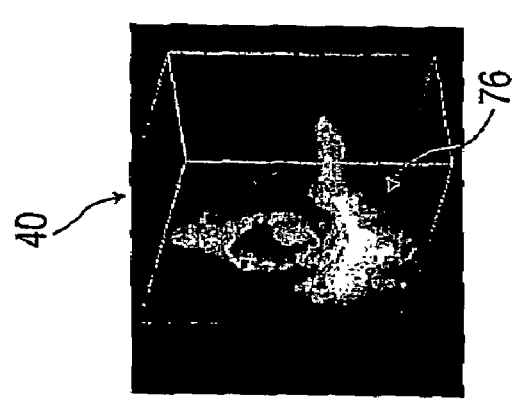
FIG. 7F
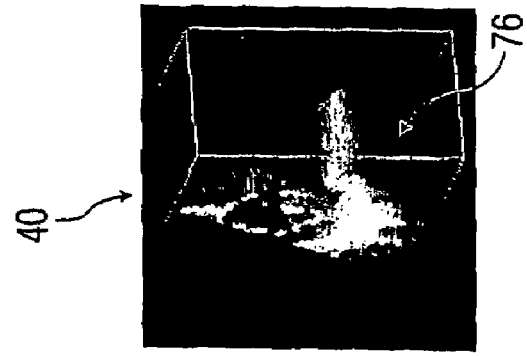
FIG. 7E
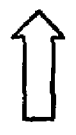
FROM 7D

SYNCHRONIZING A SWIVELING THREE-DIMENSIONAL ULTRASOUND DISPLAY WITH AN OSCILLATING OBJECT

CROSS REFERENCE TO RELATED APPLICATION

This application claims the benefit of U.S. provisional application Ser. No. 60/475,300 filed Jun. 3, 2003, which is incorporated herein by reference.

The present invention relates to ultrasound systems and their methods of operation and, in particular, to a method and system for synchronizing a swiveling or rotating three-dimensional ultrasound image with oscillations of an oscillating ultrasound object.

Diagnostic ultrasound equipment transmits sound energy into the human body and receives signals reflecting off tissue and organs such as the heart, liver, kidney, etc. Blood flow patterns are obtained from Doppler shifts or shifts in time domain cross correlation functions due to blood cell motion. These produce reflected sound waves and may be generally displayed in a two-dimensional format known as color flow imaging or color velocity imaging. Generally, the amplitudes of reflected components for structures such as the heart or vessel walls have lower absolute velocities and are 20 dB to 40 dB (10-100 times) larger than reflected components due to blood cells.

In general, an ultrasound system emits pulses over a plurality of paths and converts echoes received from objects on the plurality of paths into electrical signals used to generate ultrasound data from which an ultrasound image can be displayed. The process of obtaining the raw data from which the ultrasound data is produced is typically termed "scanning," "sweeping," or "steering a beam".

Real-time sonography refers to the presentation of ultrasound images in a rapid sequential format as the scanning is being performed. Scanning is either performed mechanically (by physically oscillating one or more transducer elements) or electronically. By far, the most common type of scanning in modern ultrasound systems is electronic wherein a group of transducer elements (termed an "array") arranged in a line are excited by a set of electrical pulses, one pulse per element, timed to construct a sweeping action.

One of the most requested features on ultrasound systems is the ability to present an image having the appearance of a three-dimensional object. Such an image is produced from a three-dimensional data matrix. This volume of data is processed to create an image for display on a two-dimensional surface that has the appearance of being three-dimensional. Such processing is typically referred to as a rendering.

While some three-dimensional optimized ultrasound systems are available, most commercial ultrasound systems today display only planar two-dimensional images, acquiring scan data from one-dimensional array probes. The SONOS 5500 sold by PHILIPS MEDICAL SYSTEMS, is one example of one such system. Some commercial systems, including the SONOS 5500, can generate three-dimensional ultrasound images with the help of "off-line" post-processing. To do this, sequences of regularly spaced planar two-dimensional sweeps are collected as the position of the probe is translated or rotated in some way between scan frames. Post-processing manipulation reconstructs three-dimensional data sets using acquired position information for each two-dimensional scan plane. The resulting three-dimensional data sets are displayed as rendered images, typically on a separate workstation, using any of various well-known, computation-intensive rendering techniques. Furthermore, the real-time rendering and display workstation may be integrated with the ultrasound scanner into one system; for example VOLUMETRICS, Inc., produces such a system.

In both true three-dimensional volumetric ultrasound systems and two-dimensional ultrasound systems that produce three-dimensional images, it is necessary to have an effective way to display the resulting three-dimensional ultrasound images. Unfortunately, the most common way of displaying ultrasound images is through a computer monitor, which generally is a two-dimensional flat screen. On a two-dimensional computer monitor display, the three-dimensional properties can be lost due to a variety of factors. One such factor is the occlusion or obstruction of portions of objects along the viewer's line of sight. Because of visual occlusion, very important aspects of an ultrasound image may be blocked from view. Such can result in a less than complete understanding of the information being displayed by the three-dimensional ultrasound image.

Another problem with the display of three-dimensional ultrasound images on a two-dimensional computer monitor relates to the phenomenon that some objects simply look differently when displayed as three-dimensional ultrasound images. Because of the need to develop a more complete understanding of what such a system is actually displaying, simply showing the three-dimensional ultrasound image on a two-dimensional computer monitor is inadequate for many diagnoses. Without the ability to manipulate the image in some way, it is far more likely that the volumetric ultrasound image will not convey to the viewer all of the possibly important information that exists in the image.

In accordance with the present invention, a method and system for synchronizing a swiveling three-dimensional ultrasound display with an oscillating ultrasound object is provided that substantially eliminates or reduces the disadvantages and problems associated with prior ultrasound image system displays.

According to one aspect of the present invention, there is provided a method for displaying a three-dimensional ultrasound image of an oscillating ultrasound object that includes the steps of forming a volumetric ultrasound image of the oscillating ultrasound object. The volumetric ultrasound image displays the oscillation of the oscillating ultrasound object The method swivels or rotates the volumetric ultrasound image from a beginning aspect through a rotation or swivel cycle. The process further synchronizes a beginning of the swivel cycle of the volumetric ultrasound image to coincide with a particular phase of an oscillation of the oscillating ultrasound object.

A technical advantage of the present invention is that it significantly improves the perception of a three-dimensional volumetric ultrasound image on a two-dimensional display or monitor by presenting to the viewer a variable display. The variable display allows the viewer to see aspects of the volumetric ultrasound image that may be otherwise occluded or blocked from view due to the two-dimensional nature of the display. A further technical advantage of the present invention includes the ability to coincide the beginning of a swivel cycle with the beginning of an oscillation of the oscillating ultrasound object. For example, an oscillating ultrasound object may be a human heart for which a physician desires to perform an ultrasound analysis. An ultrasound imaging system of the present invention, for example, can present a full volumetric or three-dimensional image of the beating human heart. The three-dimensional display, to enhance the physician's ability to extract the full benefit of the volumetric rendering of the beating human heart, swivels the ultrasound heart image according to a period that corresponds to the heart beat rate. By synchronizing the swivel period with the heart beat rate, a continuous, more readily analyzed display results. The benefits of such an improved display may be a more complete understanding of the heart's functioning. This more complete understanding will increase the likelihood of an accurate diagnosis of any associated heart malady.

A still further technical advantage of the present invention is that of synchronizing the swivel period with the oscillation rate of the oscillating ultrasound object to occur without additional equipment or significant system modification expenditures. By determining the frame rate for the ultrasound image, the total swivel cycle time, and the period of the oscillation, the present invention makes it possible to present the synchronized swivel display and ultrasound object oscillation as an integrated presentation. The presentation may be, at the viewer's discretion, that of a recorded image, a static image that is variably controllable, and a live image. The variably controllable mode appears as a paused or frozen video image, which image is controllable by a track ball or similar input device.

Other technical advantages are readily apparent to one skilled in the art from the following figures, description, and claims.

For a more complete understanding of the present invention and advantages thereof, reference is now made to the following description which is to be taken in conjunction with the accompanying drawings in which like reference numbers indicate like features and wherein.

Figure 4:
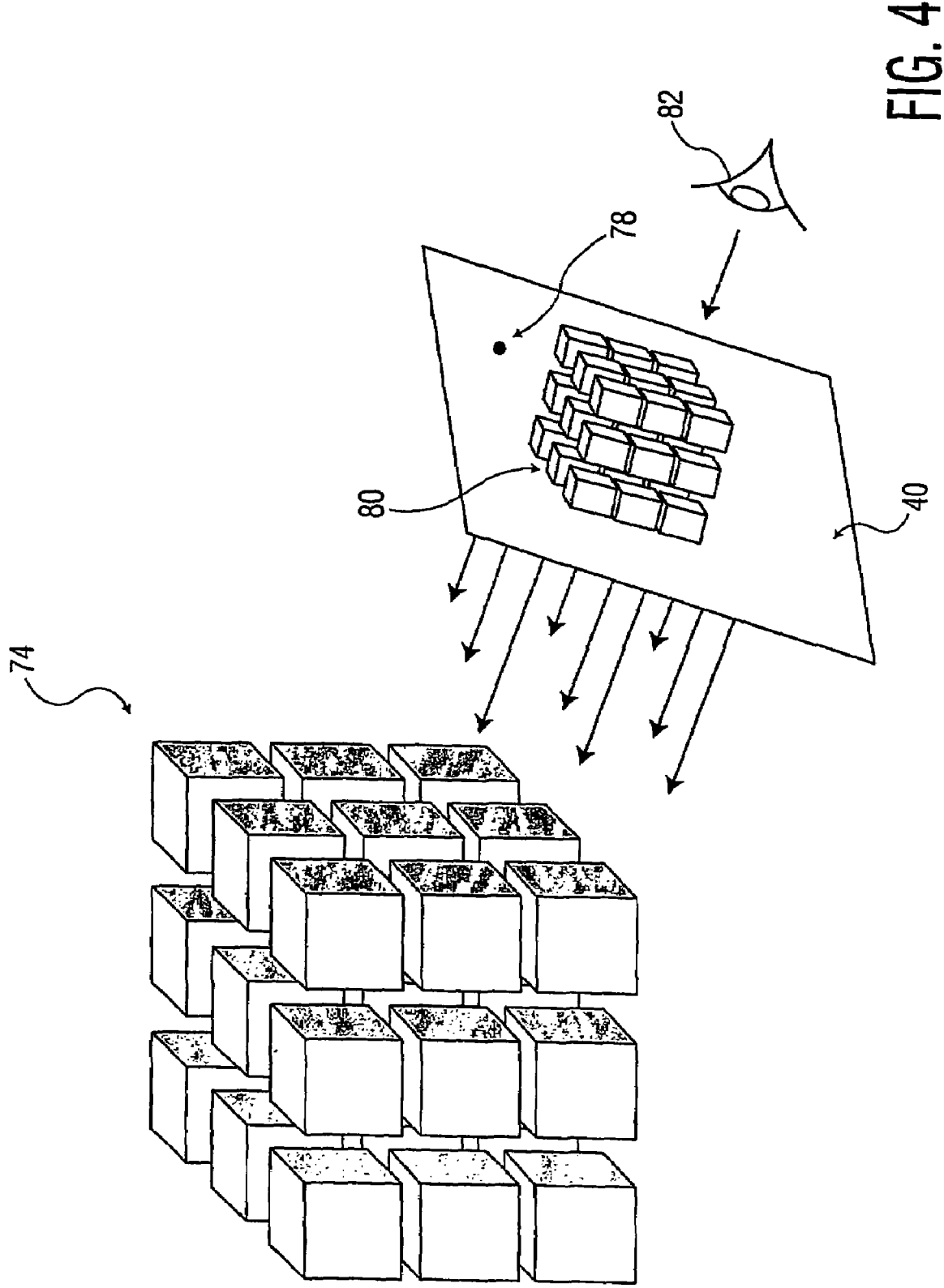
Figure 5:
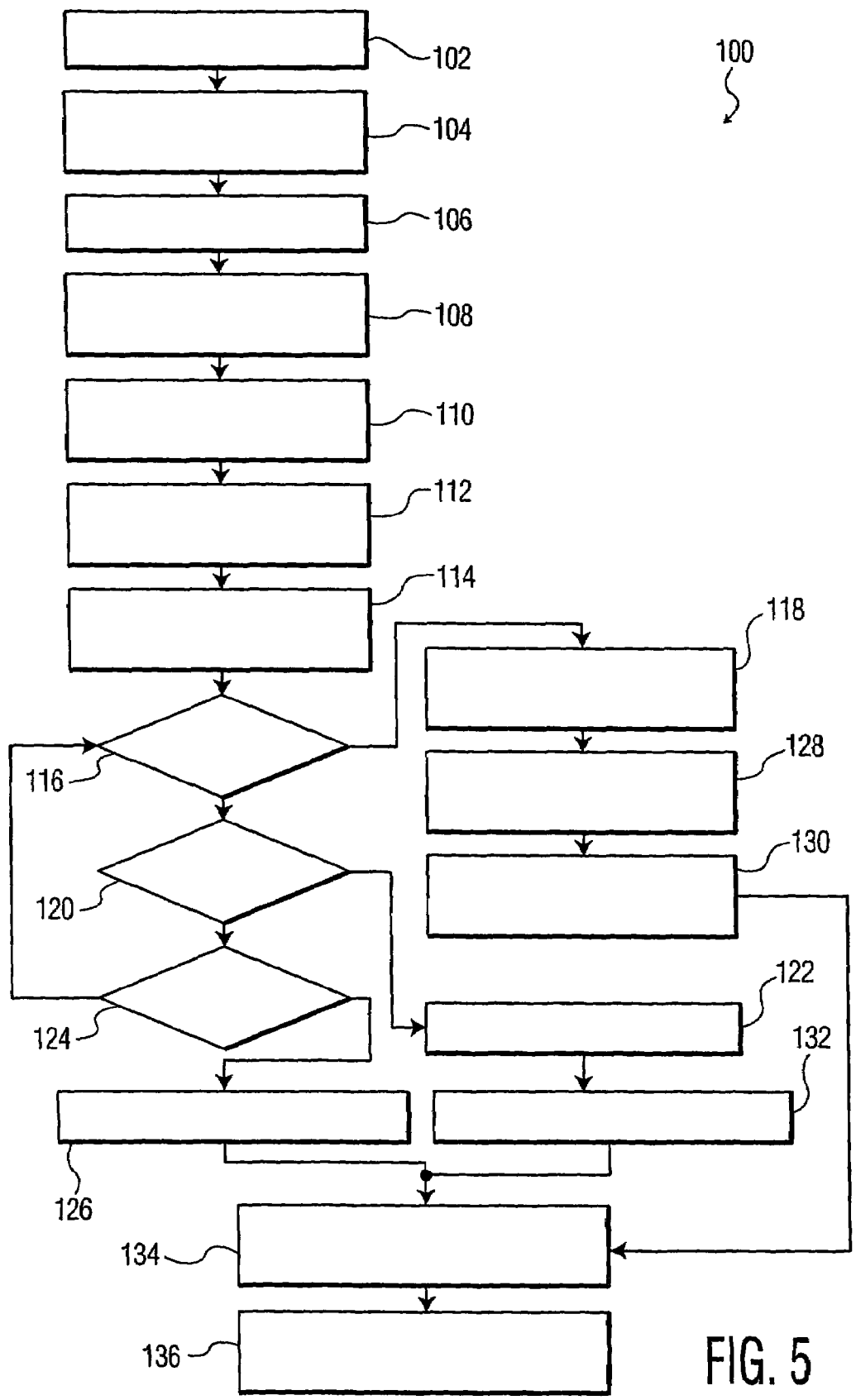

FIG. 4 portrays the challenges of creating a two-dimensional image from a three-dimensional object, which process the present invention addresses;

FIG. 5 provides an exemplary flow diagram for the synchronization process of the present invention;

FIGS. 6A through 6H show samples of the frames an ultrasound imaging system may display of an oscillating ultrasound object; and FIGS. 7A through 7G relate to the synchronization of an ultrasound image swivel display with the oscillating object according to the teachings of the present invention.

The preferred embodiment of the present invention and its advantages are best understood by referring to FIGS. 1 through 7G of the drawings, like numerals being used for like and corresponding parts of the various drawings.

Figure 1:
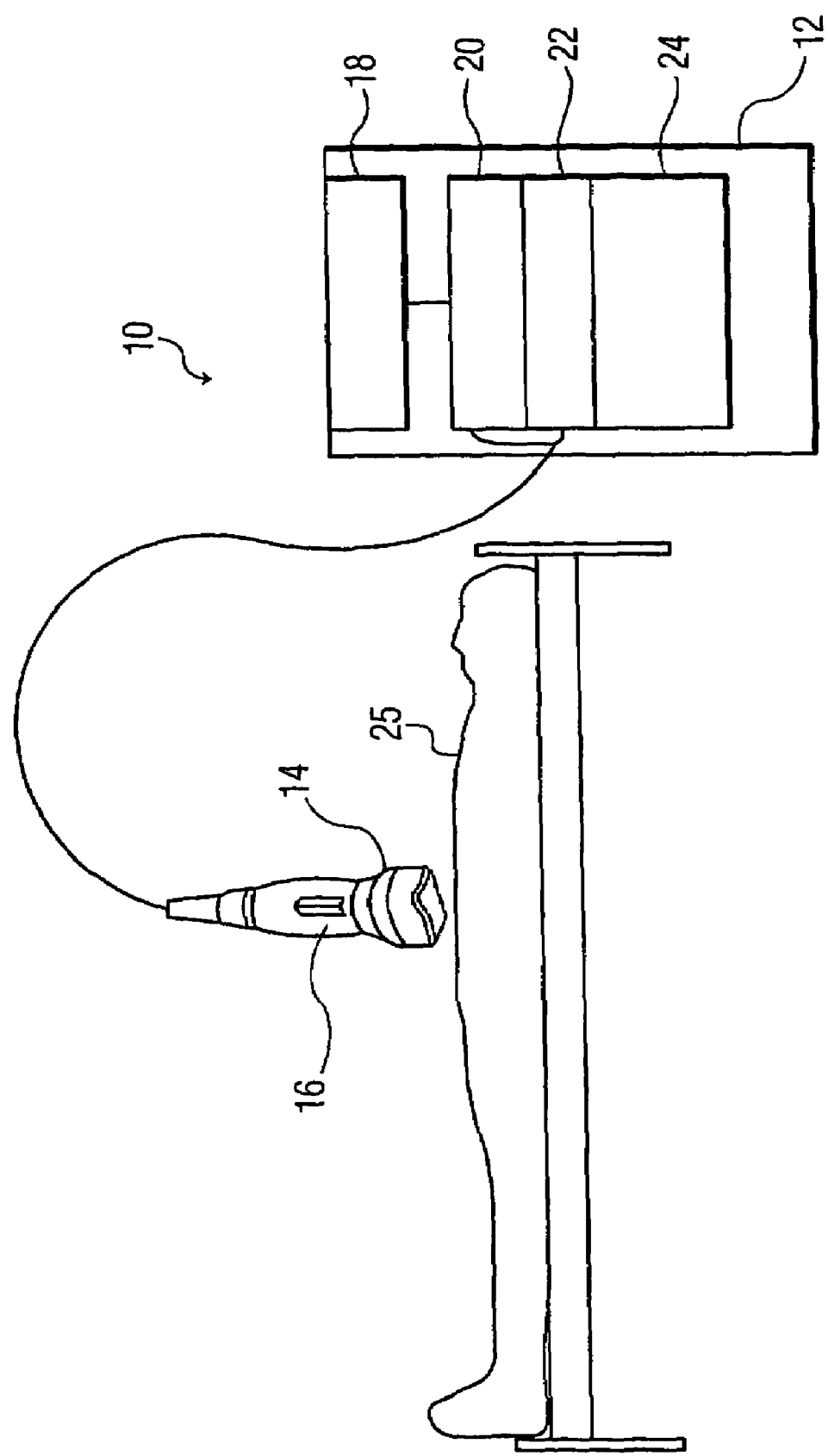
FIG. 1 is a diagram illustrating the use of an ultrasound diagnostic system that may use the present invention.

FIG. 1 shows a simplified block diagram of an ultrasound imaging system 10 that may use the concepts presented in accordance with the preferred embodiment of the present invention. It will be appreciated by those of ordinary skill in the relevant arts that ultrasound imaging system 10, as illustrated in FIG. 1, and the operation thereof as described hereinafter is intended to be generally representative of such systems and that any particular system may differ significantly from that shown in FIG. 1, particularly in the details of construction and operation of such system. As such, ultrasound imaging system 10 is to be regarded as illustrative and exemplary and not limiting as regards the invention described herein or the claims attached hereto.

In certain circumstances, when it is desirable that a piece of hardware possess certain characteristics, these characteristics are described more fully in the following text. The required structures for a variety of these machines may appear in the description given below. Machines which may be modified in accordance with the teachings of the present invention include those manufactured by such companies as PHILIPS MEDICAL SYSTEMS INTERNATIONAL, GE MEDICAL SYSTEMS, and SIEMANS MEDICAL SYSTEMS, as well as other manufacturers of ultrasound equipment.

Ultrasound imaging system 10 generally includes ultrasound unit 12 and connected transducer 14. Transducer 14 includes a receiver 16. Ultrasound unit 12 has integrated therein a transmitter 18 and associated controller 20. Controller 20 provides overall control of the system by providing timing and control functions. As will be discussed in detail below, the control routines include a variety of routines that modify the operation of receiver 16 so as to produce a volumetric ultrasound image as a live real-time image, a previously recorded image, or a paused or frozen image for viewing and analysis. Ultrasound unit 12 is also provided with imaging unit 22 for controlling the transmission and receipt of ultrasound, and image processing unit 24 for producing a display on a monitor (See FIG. 2). Image processing unit 24 contains routines for rendering a three-dimensional image.

During freehand imaging, a user moves transducer 14 over subject 25 in a controlled motion. Ultrasound unit 12 combines image data produced by imaging unit 22 with location data produced by the controller 20 to produce a matrix of data suitable for rendering onto a monitor (See FIG. 2). Ultrasound imaging system 10 integrates image rendering processes with image processing functions using general purpose processors and PC-like architectures. On the other hand, use of ASICs to perform the stitching and rendering is possible.

Figure 2:
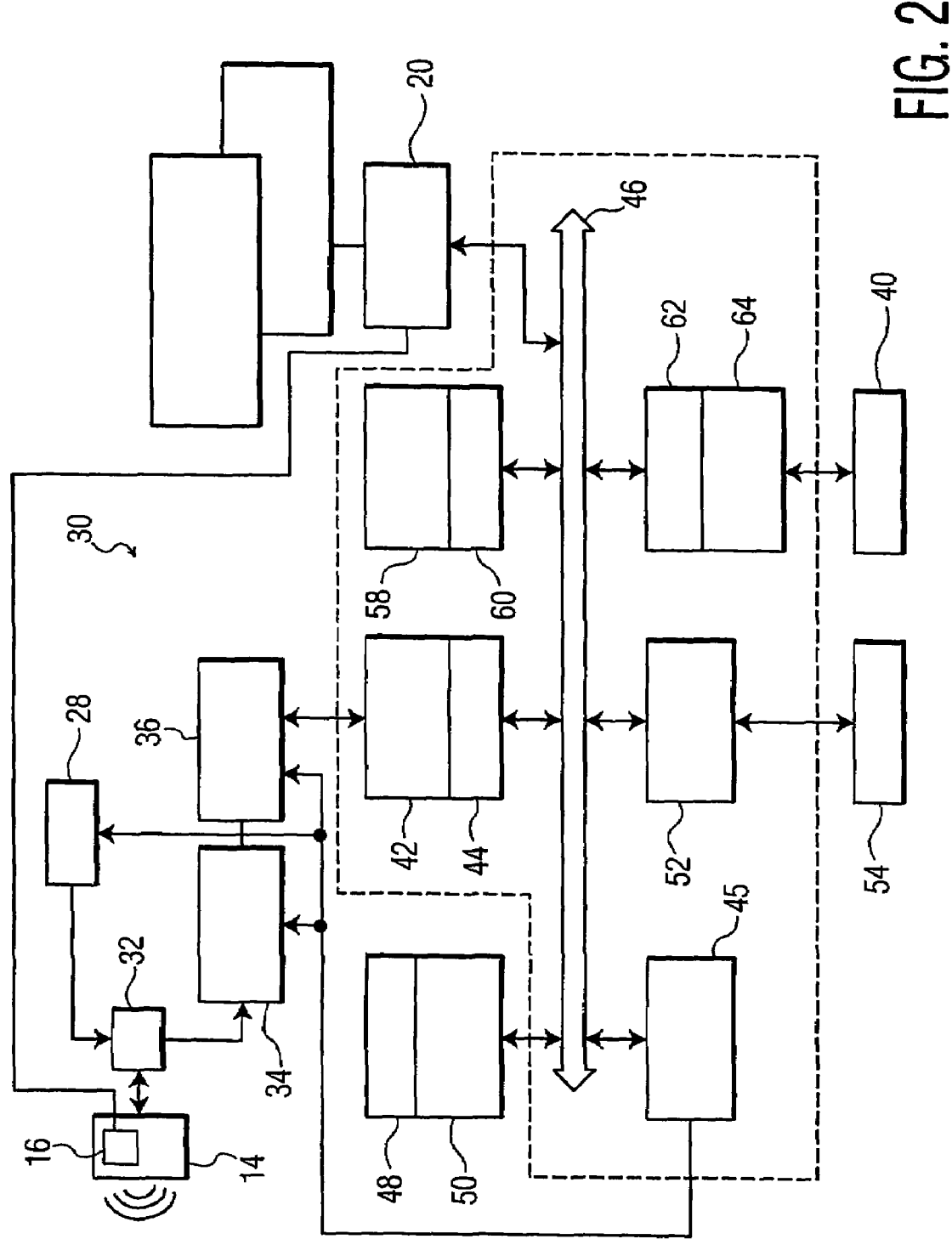
FIG. 2 is a block diagram of an ultrasound system in accordance with the preferred embodiment of the present invention.

FIG. 2 is a block diagram 30 of an ultrasound system in accordance with the preferred embodiment of the present invention. The ultrasound imaging system shown in FIG. 2 is configured for the use of pulse generator circuits, but could be equally configured for arbitrary waveform operation. Ultrasound imaging system 10 uses a centralized architecture suitable for the incorporation of standard personal computer ("PC") type components and includes transducer 14 which, in a known manner, scans an ultrasound beam, based on a signal from a transmitter 28, through an angle. Backscattered signals, i.e., echoes, are sensed by transducer 14 and fed, through receive/transmit switch 32, to signal conditioner 34 and, in turn, to beamformer 36. Transducer 14 includes elements, preferably configured as an electronically steerable two-dimensional array. Signal conditioner 34 receives backscattered ultrasound signals and conditions those signals by amplification and forming circuitry prior to their being fed to beamformer 36. Within beamformer 36, ultrasound signals are converted to digital values and are configured into "lines" of digital data values in accordance with amplitudes of the backscattered signals from points along an azimuth of the ultrasound beam.

Beamformer 36 feeds digital values to application specific integrated circuit (ASIC) 38 which incorporates the principal processing modules required to convert digital values into a form more conducive to video display that feeds to monitor 40. Front end data controller 42 receives lines of digital data values from beamformer 36 and buffers each line, as received, in an area of buffer 44. After accumulating a line of digital data values, front end data controller 42 dispatches an interrupt signal, via bus 46, to shared central processing unit (CPU) 48, which may be a MOTOROLA PowerPC. CPU 48 executes control procedures 50 including procedures that are operative to enable individual, asynchronous operation of each of the processing modules within ASIC 38. More particularly, upon receiving an interrupt signal, CPU 48 feeds a line of digital data values residing in buffer 42 to random access memory (RAM) controller 52 for storage in random access memory (RAM) 54 which constitutes a unified, shared memory. RAM 54 also stores instructions and data for CPU 48 including lines of digital data values and data being transferred between individual modules in ASIC 38, all under control of RAM controller 52.

Transducer 14, as mentioned above, incorporates receiver 16 that operates in connection with transmitter 28 to generate location information. The location information is supplied to (or created by) controller 20 which outputs location data in a known manner. Location data is stored (under the control of the CPU 48) in RAM 54 in conjunction with the storage of the digital data value.

Control procedures 50 control front end timing controller 45 to output timing signals to transmitter 28, signal conditioner 34, beamformer 36, and controller 20 so as to synchronize their operations with the operations of modules within ASIC 38. Front end timing controller 45 further issues timing signals which control the operation of the bus 46 and various other functions within the ASIC 38.

As aforesaid, control procedures 50 configure CPU 48 to enable front end data controller 44 to move the lines of digital data values and location information into RAM controller 52 where they are then stored in RAM 54. Since CPU 48 controls the transfer of lines of digital data values, it senses when an entire image frame has been stored in RAM 54. At this point, CPU 48 is configured by control procedures 50 and recognizes that data is available for operation by scan converter 58. At this point, therefore, CPU 48 notifies scan converter 58 that it can access the frame of data from RAM 54 for processing.

To access the data in RAM 54 (via RAM controller 52), scan converter 58 interrupts CPU 48 to request a line of the data frame from RAM 54. Such data is then transferred to buffer 60 of scan converter 58 and is transformed into data that is based on an X-Y coordinate system. When this data is coupled with the location data from controller 20, a matrix of data in an X-Y-Z coordinate system results. A four- (4-) dimensional matrix may be used for 4-D (X-Y-Z-time) data. This process is repeated for subsequent digital data values of the image frame from RAM 54. The resulting processed data is returned, via RAM controller 52, into RAM 54 as display data The display data is stored separately from the data produced by beamformer 36. CPU 48 and control procedures 50, via the interrupt procedure described above, sense the completion of the operation of scan converter 58. Video processor 64, such as the MITSUBISHI VOLUMEPRO series of cards, interrupts CPU 48 which responds by feeding lines of video data from RAM 54 into buffer 62, which is associated with the video processor 64. Video processor 64 uses video data to render a three-dimensional volumetric ultrasound image as a two-dimensional image on monitor 40. Further details of the processing of four dimensional cardiac data may be found in U.S. Pat. No. 5,993,390.

Figure 3:
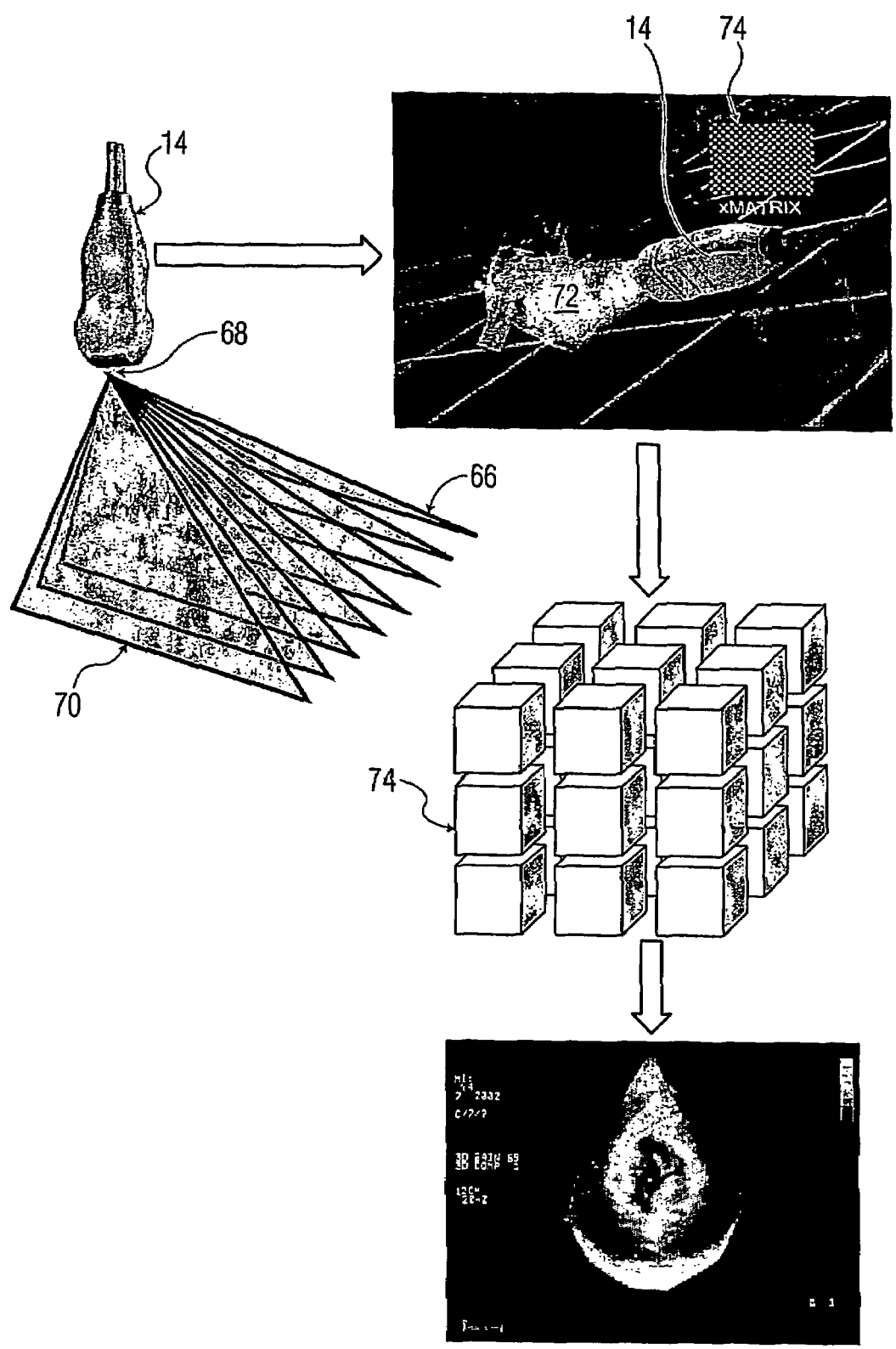
FIG. 3 shows conceptually the process of the present invention beginning with ultrasound propagation and continuing through to display of a volumetric ultrasound image on a computer monitor.

FIG. 3 shows conceptually the process of the present invention, beginning with ultrasound propagation and continuing through to the display of a volumetric ultrasound image on computer monitor 40. In the example shown in FIG. 3, there are slices 66 conjoined at single apex 68, but otherwise separated. Each of scan lines 70 in slices 66 has a matching (or "indexed") scan line in the other slices. Preferably, scan lines 70 with the same lateral position are matched across the set of slices. One way to accomplish this is to index each of the scan lines in a slice by numbering them in sequence. Then scan lines 70 having the same index value can be easily matched.

To render a volumetric three-dimensional image, data points on each of sets of matched scan lines 70 are linearly combined using an addition routine. In other words, each slice in the set of slices is accumulated in the elevation direction to produce an aggregate slice for subsequent display. Preferably, but not necessarily, the data points in each slice are weighted, for example, on a line-by-line basis by using a multiply and accumulate routine (also known as a "MAC routine").

FIG. 3 further illustrates the processing of ultrasound data, for example of human heart 72, using volumetric ultrasound processing for which the present invention has particular beneficial application. In one embodiment, the present invention has particularly beneficial use with a live, three-dimensional ultrasound architecture that instantaneously processes data from slice 66 arising from the use of transducer 14 to produce voxel matrix 74 of data Voxel matrix 74, through the use a powerful supercomputer architecture such as that of the SONOS 7500 System manufactured by Philips Medical Systems, processes within a small amount of time, nominally 50 milliseconds, streaming three-dimensional ultrasound data. This processed ultrasound data may then appear on a monitor 40 screen to show in real-time, oscillating ultrasound object 76.

The three-dimensional system such as the SONOS 7500 with which the present invention operates uses transducer 14, which includes a 3000-element array, and associated microprocessors that preprocess data using an advanced, yet PC-based, computing platform, as well as special software that allows interactive image manipulation and an easy-to-use operator interface. The 3000-element array captures data about an ultrasound object, such as the heart, as a volume. By combining a tansducer crystal that is etched to have the necessary number of crystals with a microprocessing circuit that efficiently triggers the transducer elements, the ultrasonic imaging system with which the present invention operates harnesses the computing power of more than 150 computer boards. Further details of such an array and microprocessors are described in U.S. Pat. Nos. 5,997,479; 6,013,032; and 6,126,602.

The processing architecture includes both hardware and software that allows real-time generation of volume data. This PC-based technology supports instantaneous display of three-dimensional images. With this technology, the ultrasound imaging system applies the 3000 channels to the SONOS 7500 mainframe beamformer for scanning in real time. Three-dimensional scan converter 58 processes at a rate of over 0.3 giga-voxels per second to produce image 76 from voxel matrix 74.

The present embodiment of the invention, therefore, may be employed in a three-dimensional live ultrasound imaging and display process to enhance known echocardiography analysis and diagnosis. The system with which the present invention may operate has the ability to generate and display three-dimensional images of a beating heart an instant after the data are acquired. However, the present invention may also operation with other, near-real-time three-dimensional systems which may need several seconds to acquire the data and additional time to reconstruct it as a three-dimensional ultrasound display. In such systems, data acquisition leading to three-dimensional ultrasound images of the heart may be gated for electrocardiogram and respiration analysis and diagnosis.

The system with which the present invention preferably operates delivers a full-volume view of the heart that can be rotated to allow the operator to see cardiac anatomy from several perspectives. Images can also be cropped to obtain cross-sectional pictures of complex anatomical features such as heart valves. The preferred ultrasound system for using the present invention can also provide information about a patient's heart size, shape, and anatomic relationships. Such a system is attractive to a wide range of medical environments from the community hospital and university echo lab to private offices. The three-dimensional capability of such a system allows a better appraisal of the correlation between valves, chambers, and vessels in the heart.

The live, volumetric ultrasound system with which the present invention preferably operates provides improved visualization of complex anatomic features, particularly in pediatrics. Typically in pediatrics, cardiologists spend quite a bit of time looking at various two-dimensional planes, trying to link one part of the heart to another. Volume rendering by a system of the present invention may lead to improved, faster assessment of the pediatric heart, because physicians can better visualize the heart and surrounding structures.

Volumetric rendering coupled with the swiveling display of the present invention, permits a viewer to manipulate the data set in space, rotate the image while maintaining a chosen perspective, and thereby provide clarity to the structural orientation of the pathology. The combination of controllable live, volumetric ultrasound imaging and the synchronized swiveling or rotating provided by the present invention enhances the likelihood of obtaining the view most likely to provide the right answer more quickly. This is because the viewer has information that he would otherwise not possess.

The combination of synchronized swiveling display and volumetric rendering has demonstrated several other potential advantages during the early testing. The present invention may allow more accurate assessment of valvular function. The ability to deliver in real-time many and changing two-dimensional displays of volumetrically rendered three-dimensional images may be helpful during catheter guidance. Moreover, the enhanced display of the present invention may provide performance improvements when assessing regional and global cardiac functions, as well as improve productivity by shortening the time for data acquisition and interpretation.

FIG. 4 introduces the challenge of using the volumetrically-rendered three-dimensional ultrasound image using a two-dimensional screen such as that of computer monitor 40. As FIG. 4 depicts, voxel matrix 74 has been created as a true volumetric rendering of an ultrasound object, such as beating human heat 72. Monitor 40 includes an array of pixels 78 which are differentially energized and controlled by ultrasound imaging system 10. Without the process of the present invention, occlusion and imperfections associate with attempting to convey three-dimensional data form voxel matrix 74 on two-dimensional monitor 40 as image 80. This may prevent viewer 82 from appreciating the benefits of the processing and data capture which ultrasound imaging system 10 can provide.

The present invention, therefore, provides a process that overcomes the depth perception and other related problems of volumetric imaging. To overcome the depth perception problem, the present invention takes into consideration the fact that, because the image is a fully volumetrically-rendered ultrasound image, it is possible to variably display the image from a wide variety of angles on monitor 40. Moreover, the present invention acknowledges that, with an oscillating object, such as beating heart 72, it is possible to further enhance the three-dimensional perception of the oscillating ultrasound object. Accordingly, the present invention provides a process for both taking advantage of the many angles in three-dimensional space through which an ultrasound object may be viewed and the fact that some ultrasound objects, by their very nature, oscillate, vibrate, or otherwise repeatedly or cyclically move. This combination results in the synchronization of the swivel or rotation cycle in the volumetric ultrasound image with the oscillation or beating movement of the ultrasound object.

FIG. 5, therefore, provides an exemplary flow diagram for the synchronization process of the present invention. In brief, the method includes the steps of forming a volumetric ultrasound image of an oscillating ultrasound object. The volumetric ultrasound image displays the oscillation of the oscillating ultrasound object. In this embodiment the display repetitively rotates the volumetric ultrasound image from a beginning aspect through a swivel or rotation cycle, with the swivel or rotation returning to the beginning aspect. The process synchronizes a beginning of the repetitive rotation of the volumetric ultrasound image to coincide with the beginning of an oscillation of the oscillating object.

The process 100 begins on a system such as the SONOS 7500, by determining at step 102 if the viewer has enabled the system's swiveling action display. Only if the swivel process is enabled will the ultrasound image system employ the synchronization process. The synchronization process 100 begins with calculating the number of times an oscillation should be replayed for the given swivel cycle at step 104. This includes determining the frame rate in hertz or frames per second for the given ultrasound display system at step 106. Then, the process obtains the number of frames (i.e., single volumes) contained in an oscillation of the oscillating ultrasound object at step 108. The process then calculates the total time in seconds that it would take to repeat one oscillation at step 110. This is done by dividing the number of frames in an oscillation by the frame rate in frames per second of the ultrasound display system.

The process then calculates how many times to repeat the oscillation display for a single three-dimensional swivel cycle at step 112. In the preferred embodiment a nominal period of five seconds has proven effective and simple to generate for the swivel cycle period. At this step, some rounding may occurs in this process as through the use of known rounding functions that may exist in the appropriate computer language in use for the process. In essence, this calculation involves dividing the value of the number of frames for the oscillation cycle into the number of frames for the swivel cycle. To assure that the display of the swivel cycle terminates at the end of the last oscillation in the display, the period of the swivel cycle is set to terminate at the end of the last oscillation occurring in during the swivel period.

For example, if a beating heart beats at a rate of 0.7 second per beat, then seven of such beats will occur in 4.9 seconds. Therefore, to have the end of the last beat occur at the end of the swivel cycle, the swivel period is set to 4.9 seconds. At 4.9 seconds, therefore, the volumetric ultrasound display will return to the same beginning aspect. In the present embodiment there are three modes where the three-dimensional swivel display may be active. These include a replay mode, a freeze mode, and a live mode. Other names for these modes may be, for example, the cine loop mode, the pause mode or the acquiring mode. In a live mode, a continuous stream of new volumetric ultrasound data is displayed on ultrasound imaging system 10. Also, during this operational mode, the present invention may collect data that may be later displayed. In the freeze mode, either live or replay mode is stopped for the display. This is similar to the pause function of a video cassette recorder. The variably controllable mode appears as a paused or frozen video image, which image is controllable by a track ball or similar input device. In the replay mode, a recorded volumetrically rendered ultrasound image is played from the memory associated with ultrasound imaging system 10.

Process 100 of the present invention, therefore, determines in which of these modes the viewer has directed ultrasound imaging system 10 to operate at step 114. If the system has been directed to operate in the replay mode, as tested by query 116, then process flow goes to step 118. Otherwise, query 120 tests whether the viewer has directed ultrasound imaging system 10 to operate in the freeze mode. Is so, then the process flow goes to step 122, where the ultrasound image rendering rate of 10 Hz is established. Otherwise, process 100 tests whether the viewer has controlled ultrasound imaging system 10 to operate in the live mode at query 124. If so, process control goes to step 126, where a nominal swivel cycle length is established. Otherwise, the present embodiment of the invention controls process flow to return to query 116, but now with the default that the viewer has directed ultrasound system 10 to operate in the replay mode.

In the replay mode, step 118 of the process calculates the number of frames in an oscillation. Step 128 determines how many times an oscillation should be played in a swivel cycle. This is determined by calculating the total number of complete oscillations that may fit within a set swivel period. So, for example, an oscillation lasting 0.7 seconds may be completely repeated in a swivel period of five (5) seconds a total of seven (7) times, with a remainder of one (1) second. Or, equivalently, in 4.9 seconds exactly seven (7) complete oscillations (i.e., seven (7) complete periodic heart cycles) will occur. Further, the process calculates, at step 130, the number of frames required to achieve the desire swivel period duration. This is done simply by multiplying the number of frames per oscillation by the number of oscillations in the swivel period. This determines the number of frames to use for the swivel. So, for example, if the volumetric ultrasound display rendered at a rate of 20 Hz, then in an oscillation period of 0.7 seconds there would be 14 (=20 Frames/sec×0.7 sec/oscillation) frames per oscillation. This would call for 98 (=14 frames/oscillation×7 oscillations/swivel period) frames to be used in the swivel period. Accordingly, from the beginning aspect of the volumetric ultrasound image through the entire swivel range and back to the beginning aspect should use 98 frames from ultrasound imaging system 10 on monitor 40. This will assure that all swivel periods begin and end at the same aspect. Furthermore, the swivel period is divided into 98 phases, such that each phase, corresponding to a unique frame, is displayed at a slightly different viewing angle.

In the live mode, the ultrasound system acquires live ultrasound data. This may use a default number of frames for the live data at step 126. This would permit a simplification of the display when actually acquiring live info. Alternatively, the number of frames observed for a given oscillation can be used for the purpose of providing a volumetric ultrasound image display that achieves the same beginning and ending aspects as described above.

In the pause mode, i.e., during either the live or cine loop mode being paused, the display will be presented in a period of 10 Hz. This may be a variably static display through which the viewer has control of the aspect angle of the volumetric ultrasound image. The swivel display may be set at five (5) seconds with a refresh interval of 100 milliseconds, for example. Also, in the freeze mode, the system determines where to use the nominal swivel period as is used in the live mode at step 132.

The process further controls the three-dimensional swivel angle at step 134. For example, in the present embodiment the horizontal range may be +/−50 degrees with a vertical angle of 0 degrees. Moreover, at step 136, the present embodiment provides a way to smooth both the swivel display and the appearance of the oscillation on monitor 40. There may be other ways of changing the swivel angle and display. Moreover, the process of FIG. 5 is intended to be only exemplary, for there may be many different ways of implementing the novel concepts of the present invention while deviating from the precise steps of the FIG. 5 flowchart.

In order to demonstrate the benefits of the present invention FIGS. 6A through 6H and 7A through 7G demonstrate the synchronization of an ultrasound image swivel display with the oscillating object according to the teachings of the present invention. In FIGS. 6A through 6H, a series of volumetric ultrasound images of a beating human heart 72 appear as an oscillating ultrasound object. In this example, human heart 72 beats at a rate of 0.7 seconds per beat. Thus, if ultrasound imaging system 10 renders a volumetric ultrasound image at a rate of 20 Hz, then each beat consumes 14 frames. Accordingly and showing only the relevant odd-numbered frames, FIG. 6A shows a volumetric ultrasound image of the heart at a Frame 1 occurring at 0.00 sec, FIG. 6B an image at a Frame 3, which occurs at 0.15 sec, FIG. 6C shows the Frame 5 occurring at 0.25 sec, on to FIG. 6G of the Frame 13 occurring at 0.65 seconds. Note that FIG. 6H shows Frame 15, which is similar to Frame 1 of FIG. 6A, since the human heat 72 has begun a new oscillation or beat. However, notice further that, since image 76 is swiveling, the aspect or view of image 76 has changed. Thus, FIGS. 6A through 6G would show a complete oscillation or beat for the beating human heart, with FIG. 6H showing the beginning of a new oscillation or beat.

FIGS. 7A through 7G relate to the synchronization of an ultrasound image swivel display with the oscillating object according to the teachings of the present invention. Thus, FIGS. 7A through 7G show progressive images of the human heart through a single swivel or rotation period. Based on the period, 0.7 seconds, for a complete heart beat, and the initially nominal swivel period of five (5) seconds, a total of seven (7)(=(5.0 seconds/swivel period)/(0.7 seconds/oscillation)) oscillations or heat beats are called for in the swivel period. Thus, FIG. 7A shows the beginning heart beat of the seven heart beats concluding at 0.7 sec. FIG. 7B shows the second heart beat concluding at 1.4 sec. Continuing at 0.7 second intervals, the swivel rotation concludes at FIG. 7G which shows the final heart beat at 4.9 sec.

Note that in the progressive views of FIGS. 7A through 7G, while the aspect of the ultrasound object changes, the stage of the ultrasound object in its oscillation does not change as significantly. The previous FIGS. 6A through 6H, however, show that the appearance of the heart valve changes significantly during its beating. Note that the phenomena of the heart not changing significantly from the beginning aspect of the swivel period and the ending aspect of the swivel period and the positions of the beginning aspect and ending aspect being essentially the same provides for significant flexibility in both recording and playing back recorded volumetric ultrasound images.

One benefit of the present invention is that existing hardware and software can be easily modified to produce the required images. For example, using controls which are already available on the SONOS 7500, images in accordance with the present preferred embodiment can be produced without any changes to the hardware.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

The invention claimed is:

1. A method for displaying three-dimensional ultrasound image data representing an oscillating object, comprising the steps:

forming a volumetric ultrasound image of an oscillating object, said volumetric ultrasound image for displaying the oscillation of said oscillating object;

rotating the volumetric ultrasound image from a beginning aspect through a rotation period;

synchronizing a beginning of the rotation period of the volumetric ultrasound image to coincide with the beginning of an oscillation of the oscillating object; and displaying on a two-dimensional display a three-dimensional perception of said volumetric ultrasound image of said oscillating object.

2. The method of claim 1, wherein said rotating step comprises the step of swiveling the volumetric ultrasound image from a beginning swivel aspect through a swivel cycle, said swivel cycle returning the volumetric ultrasound image of the oscillating object to said beginning swivel aspect.

3. The method of claim 1 further comprising the step of controllably displaying said volumetric ultrasound image from a plurality of three-dimensional directions.

4. The method of claim 1, further comprising the step of forming a volumetric ultrasound image of a beating heart, wherein said oscillation corresponds to the beating of said beating heart.

5. The method of claim 4, further comprising the step of controllably displaying said beating heart as a real-time volumetrically rendered ultrasound image.

6. The method of claim 4, further comprising the step of controllably displaying said beating heart as a previously recorded volumetrically rendered ultrasound image.

7. The method of claim 4, further comprising the step of controllably displaying said beating heart as a static volumetrically rendered ultrasound image.

8. The method of claim 7, wherein the static volumetrically rendered ultrasound image comprises a variably-controllable, static, volumetrically rendered ultrasound image, the method further comprising displaying said variably-controllable, static, volumetrically rendered ultrasound image of the beating heart such that the beginning aspect of the variably-controllable, static, volumetrically rendered ultrasound image of said beating heart corresponds to a stage of said beating heart at some point in the beating.

9. The method of claim 8 further comprising the step of volumetrically rendering said variably-controllable, static, volumetrically rendered ultrasound image of said heart at a rate of not less than 10 Hz.

10. The method of claim 8 further comprising the step of controllably changing a view of the variably-controllable, static, volumetrically rendered ultrasound image of said heart using a three-dimensional positioning control system.

11. The method of claim 1, further comprising the steps of:

forming said volumetric ultrasound image of the oscillating object as a real-time volumetric ultrasound image; and recording said rotating volumetric ultrasound image of said oscillating object for forming a recorded volumetric ultrasound image having a property that repeated continuous playing of said recordings appear as a continuous oscillating display of said oscillating object.

12. A system for displaying a three-dimensional ultrasound image of an oscillating object, the system comprising:

a processing device including at least one processor and at least one memory device storing instructions to be executed by the at least one processor, the processing device being configured to execute an algorithm including:

forming a volumetric ultrasound image of an oscillating object, said volumetric ultrasound image for displaying the oscillation of said oscillating object;

rotating the volumetric ultrasound image from a beginning aspect through a rotation;

synchronizing a beginning of the rotation of the volumetric ultrasound image to coincide with the beginning of an oscillation of the oscillating object; and displaying on a two-dimensional display a three-dimensional perception of said volumetric ultrasound image of said oscillating object.

13. The system of claim 12, wherein the algorithm executed by the processing device further comprises swiveling the volumetric ultrasound image from a beginning swivel aspect through a swivel cycle, said swivel cycle returning the volumetric ultrasound image to said beginning swivel aspect.

14. The system of claim 12, wherein the algorithm executed by the processing device further comprises controllably displaying said volumetric ultrasound image from a plurality of three-dimensional directions.

15. The system of claim 12, wherein the algorithm executed by the processing device further comprises forming a volumetric ultrasound image of a beating heart, wherein said oscillation corresponds to the beating of said beating heart.

16. The system of claim 15, wherein the algorithm executed by the processing device further comprises controllably displaying said volumetric ultrasound image of the beating heart as a real-time volumetrically rendered ultrasound image.

17. The system of claim 15, wherein the algorithm executed by the processing device further comprises controllably displaying said volumetric ultrasound image of the beating heart as a previously recorded volumetrically rendered ultrasound image.

18. The system of claim 15, wherein the algorithm executed by the processing device further comprises controllably displaying said volumetric ultrasound image of the beating heart as a static volumetrically rendered ultrasound image.

19. The system of claim 18, wherein the static volumetrically rendered ultrasound image comprises a variably-controllable, static volumetrically rendered ultrasound image, the algorithm further comprising displaying said variably-controllable, static, volumetrically rendered ultrasound image of the beating heart such that the beginning aspect of the variably-controllable, static, volumetrically rendered ultrasound image of the image of said beating heart corresponds to a stage of said beating heart at some point in the beating.

20. The system of claim 19, wherein the algorithm executed by the processing device further comprises volumetrically rendering said variably-controllable, static, volumetrically rendered ultrasound image of the of said heart at a rate of not less than 10 Hz.

21. The system of claim 19, wherein the algorithm executed by the processing device further comprises controllably changing a view of said variably-controllable, static, volumetrically rendered ultrasound image of the of said heart using a three-dimensional positioning control system.

22. The system of claim 12, wherein the algorithm executed by the processing device further comprises:

forming said volumetric ultrasound image of the oscillating object as a real-time volumetric ultrasound image; and recording said rotating volumetric ultrasound image of said oscillating object for forming a recorded volumetric ultrasound image having a property that repeated continuous playing of said recordings appear as a continuous non-repetitive display of said oscillating object.

23. A tangible. processor-readable, storage medium storing instructions that are executable by at least one processor for forming an ultrasound image synchronizing system for displaying a three-dimensional ultrasound image of an oscillating object, said stored instructions comprising:

volumetric ultrasound image forming instructions for forming a volumetric ultrasound image of an oscillating object, said volumetric ultrasound image for displaying the oscillation of said oscillating object;

rotating instructions for rotating the volumetric ultrasound image from a beginning aspect through a rotation;

synchronizing instructions for synchronizing a beginning of the rotation of the volumetric ultrasound image to coincide with the beginning of an oscillation of the oscillating object; and displaying instructions for displaying said oscillating object on a two-dimensional display for presenting the three-dimensional perception of said volumetric ultrasound image of said oscillating object.

24. The storage medium of claim 23, wherein said stored instructions further comprise:

image forming instructions for forming said volumetric ultrasound image of the oscillating object as a real-time volumetric ultrasound image; and recording instructions for recording said rotating volumetric ultrasound image of said oscillating object for forming a recorded volumetric ultrasound image having the property that repeated continuous playing of said recordings appear as a continuous display of said oscillating object.

25. A method for displaying three-dimensional ultrasound image data representing an oscillating object, the method comprising:

forming a volumetric ultrasound image of an oscillating object, said volumetric ultrasound image for displaying the oscillation of said oscillating object;

rotating the volumetric ultrasound image from a beginning aspect through a rotation period; and displaying the rotating volumetric ultrasound image on a display device.

26. The method of claim 25, wherein said rotating step comprises swiveling the volumetric ultrasound image from a beginning swivel aspect through a swivel cycle, said swivel cycle returning the volumetric ultrasound image of the oscillating object to said beginning swivel aspect.

27. The method of claim 25, further comprising controllably displaying said volumetric ultrasound image from a plurality of three-dimensional directions.

28. The method of claim 25, further comprising forming a volumetric ultrasound image of a beating heart, wherein said oscillation corresponds to the beating of said beating heart.

* * * * *